United States Patent [19]

Silvestrini

[11] 4,131,675

[45] Dec. 26, 1978

[54] USE OF COMBINATIONS OF L-DOPA WITH TRAZODONE AND L-DOPA WITH ETOPERIDONE IN PARKINSONISM

[75] Inventor: Bruno Silvestrini, Rome, Italy

[73] Assignee: Aziende Chimiche Riunite Angelini Francesco A.C.R.A.F. S.p.A., Rome, Italy

[21] Appl. No.: 876,383

[22] Filed: Feb. 9, 1978

[51] Int. Cl.² ................. A61K 31/195; A61K 31/495
[52] U.S. Cl. ..................................... 424/250; 424/319
[58] Field of Search ................................ 424/250, 319

[56] References Cited

U.S. PATENT DOCUMENTS

| | | | |
|---|---|---|---|
| 3,984,545 | 10/1976 | Frils, Jr. et al. | 424/319 |
| 3,988,461 | 10/1976 | Kosóczky et al | 424/319 |
| 3,991,207 | 11/1976 | Sarges et al. | 424/319 |
| 4,021,555 | 3/1977 | Seyfried et al. | 424/319 |

OTHER PUBLICATIONS

Agnoli, Stato Attuale Delle Esperienze Clenico Farmacologeche (10-4-75), pp. 142-155.

*Primary Examiner*—Stanley J. Friedman
*Attorney, Agent, or Firm*—Ladas, Parry, Von Gehr, Goldsmith & Deschamps

[57] ABSTRACT

A combination of trazodone or etoperidone with L-DOPA is used in the treatment of Parkinsonism by oral administration to a patient.

4 Claims, 2 Drawing Figures

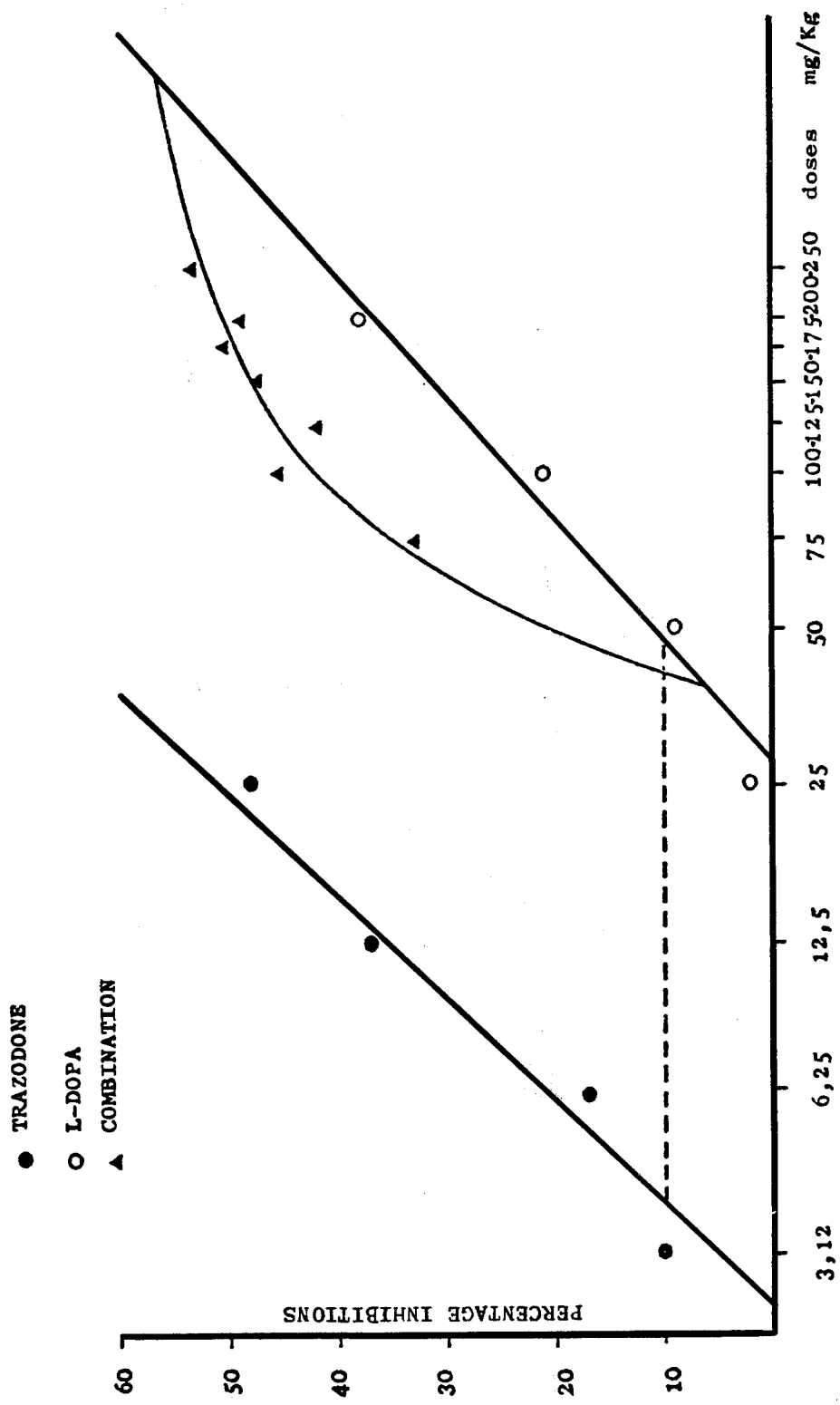
FIG. 1 - EFFECTS OF TRAZODONE AND L-DOPA, BOTH ALONE AND COMBINED ON OXOTREMORINE INDUCED TREMOR

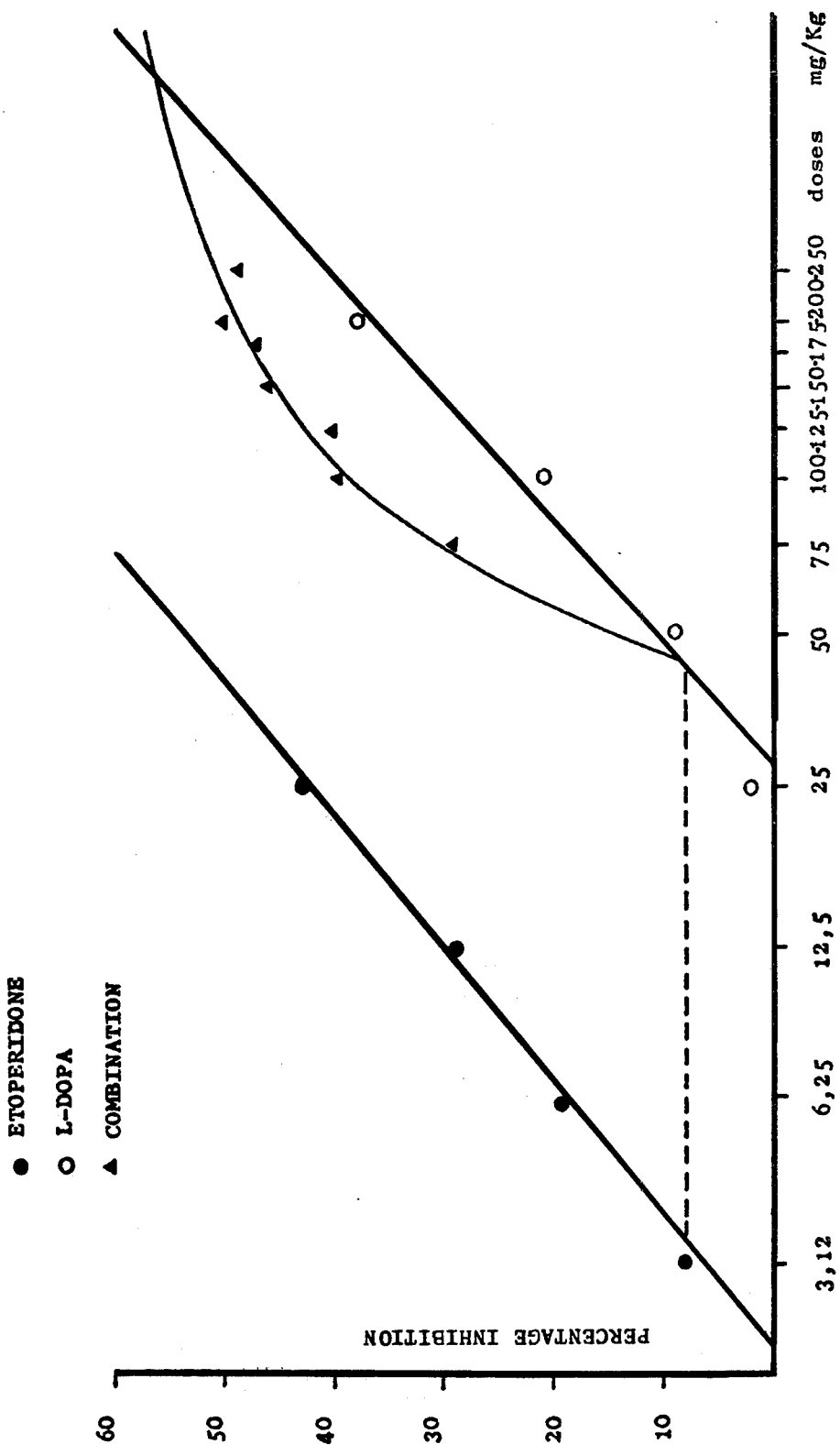
FIG. 2 - EFFECTS OF ETOPERIDONE AND L-DOPA, BOTH ALONE AND COMBINED ON OXOTREMORINE INDUCED TREMOR

USE OF COMBINATIONS OF L-DOPA WITH TRAZODONE AND L-DOPA WITH ETOPERIDONE IN PARKINSONISM

This invention concerns the use of combinations of L-DOPA with trazodone or L-DOPA with etoperidone in Parkinsonism in order to avoid the side effects of L-DOPA resulting from stimulation of the adrenergic system and improve its therapeutic action.

BACKGROUND OF THE INVENTION

L-DOPA is extensively used in the therapy of Parkinsonism. Its use is based on the well known theory that Parkinsons disease and related conditions are produced by an imbalance between dopaminergic and cholinergic mechanisms at the nigrostriatal level. Parkinsonian symptoms appear when the cholinergic mechanism prevails over the dopaminergic one. Since L-DOPA is a precursor of dopamine and potentiates the adrenergic system, it readjusts the above mentioned imbalance thus leading to an improvement in Parkinsonism. See in this respect "The Pharmacological Basis of Therapeutics", L. S. Goodman and A. Gilman, Fourth Edition, The MacMillan Company, 1970, page 423. At the same time its administration produces side effects indicative of activation of the adrenergic system such as stimulation of the central nervous system, blood pressure and ECG changes, etc.

Trazodone is a drug with the following chemical structure:

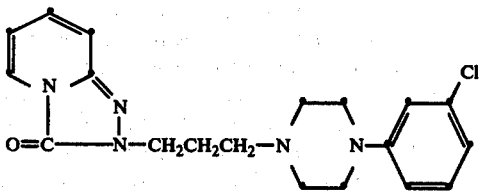

Trazodone is the subject of U.S. Pat. No. 3,381,009 and Japanese Pat. No. 555,140 in which the drug's pharmacological and therapeutic properties are attributed to its tranquilizing, hypotensive and analgesic actions.

U.S. Pat. application Ser. No. 748,421 has also been presented in the U.S. for the use of trazodone in acute vascular diseases, such as stroke.

Another Pat. application Ser. No. 793,336 has been presented in the U.S. for the use of trazodone in the treatment of tremors in Parkinsonian and other extrapyramidal syndromes.

Etoperidone is a drug with the following chemical structure:

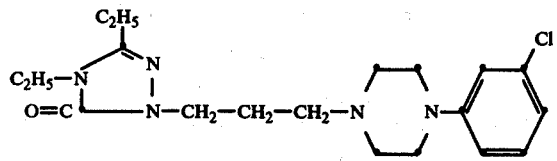

Etoperidone is the subject of U.S. Pat. No. 3,857,845 in which the drug's pharmacological and therapeutic properties are attributed to its tranquilizing, hypotensive and analgesic actions.

A new Pat. application Ser. No. 793,336 (the same as the one mentioned above for trazodone) has also been presented in the U.S. for the use of etoperidone in the treatment of tremor in Parkinsonian and other extrapiramidal syndromes.

DESCRIPTION OF THE PRIOR ART

L-DOPA, trazodone and etoperidone are known to have antiparkinsonian effects. L-DOPA is effective against rigidity and tremor which represent the main symptoms of parkinsonism, but its activity against rigidity prevails. L-DOPA also produces signs of stimulation of the adrenergic system, which are a different expression of the same mechanism of action as responsible for its therapeutic effects. The general use of trazodone and/or etoperidone as anti-parkinsonian agents is as yet only known to this Applicant. Trazodone and etoperidone are effective against tremor. It is also known that trazodone and etoperidone have adrenolytic effects.

SUMMARY OF THE INVENTION

The invention claimed in the present application was not foreseen in the prior art for the following reasons. L-DOPA is a precursor of dopamine and stimulates the adrenergic system; this mechanism of action is responsible for both its therapeutic effects in Parkinsonism and its side effects consisting of stimulation of the adrenergic system. See in this respect "The Pharmacological Basis of Therapeutics", L. S. Goodman and A. Gilman, Fourth Edition, The MacMillan Company, 1970, page 423 and in "Drugs of Choice"1976-1977, Walter Modell Ed. the articles A. Barbeauand F. McDowell, Levodopa and parkinsonism, Philadelphia, 1970, F. A. Davis Co; G. C. Cotzias, P. S. Papavasiliou and R. Gellene, Modification of parkinsonism-chronic treatment with L-DOPA, New Eng. J. Med. 280:337-345, 1969; F. H. McDowell, J. E. Lee, T. Swift, et al. Treatment of Parkinson's syndrome with L-dihydroxyphenylalanine (levodopa), Ann. Intern. Med. 72:-29-35, 1970; and M. D. Yahr, R. C. Vuvoisin, M. J. Schear et al. Treatment of parkinsonism with levodopa, Arch. Neurol. (Chicago) 21:343-354, 1969. On the other hand trazodone and etoperidone have adrenolytic effects, "Pharmacological Properties of AF1161, A New Psycotropic Drug", B. Silverstrini, V. Cioli, S. Burberi and B. Catanese, Int. J. Neuropharmacol, 1968, 7, 587–599 Pergammon Press and "Pharmacological Investigations on Etoperidone, A New Psychotropic Agent", R. Lisciani, A Baldini, G. deFeo, and B. Silvestrini, Arzneim Forschung, in Press, copy attached. Accordingly, it was expected that trazodone and etoperidone would diminish not only the side effects of L-DOPA but also its therapeutic action. Our studies, however, have shown that the combinations of L-DOPA with trazodone or L-DOPA with etoperidone not only reduce the side effects of L-DOPA, but produce a stronger therapeutic action.

EXPERIMENTAL

The experiments were conducted on CF1 mice weighing 20-25 g.

Trazodone and etoperidone in combination with L-DOPA were given orally 5 min. prior to the intraperitoneal administration of oxotremorine at the dose of 1 mg/kg s.c. The effects of the drugs on oxotremorine administration were scored according to Silvestrini and Lisciani, B. Silvestrini, R. Lisciani, Experimental data suggesting an adrenergic mechanism in the production of Parkinsonian symptoms, Curr. Ther. Res. 20, 716-724, 1976. Joint drug action was evaluated according to the method of Fedeli et al., L. Fedeli, L. Meneghini, F. Sangiovanni, F. Scrollini, E. Gori, Quantitative evaluation of joint drug action In "Toxicological problems of drug combination", Eds.: S. B. Baker and G. A. Neuhaus — International Congress Series No. 254, Excerpta Medica, Amsterdam, 231-245, 1972.

The general effects on behavior and the signs of adrenergic stimulation were studied according to the method of Irwin, S. Irwin In "Pharmacologic techniques in drug evaluation", Eds.: J. H. Nodine and P. E. Siegler, Year Book Medical Publishers, Chicago, 36-54, 1964. The $LD_{50}$ was determined by the method of Litchfield and Wilcoxon, Litchfield, J. T. Wilcoxon, F. A., J. Pharmacol Exp. Ther. 96, 99 (1949), by considering the deaths produced during the 2 weeks following administration of the drugs. The effects of drug combinations were studied according to Berkowitz and Spector, B. Berkowitz, S. Spector, The role of brain serotinin in the pharmacologic effects of the methyl xanthines — In "Serotonin and Behavior", Eds.: J. Barchas and E. Usdin, Academic Press, New York and London, 137-147, 1973.

The effects of trazodone and etoperidone on the signs of adrenergic stimulation produced by L-DOPA were studied by considering piloerection and mydriasis which represent the most typical expressions of adrenergic stimulation. The fact that adrenergic drugs produce mydriasis and piloerection is generally known, see, for example, "Physiological Basis of Medical Practice" by Best & Taylor, Ed. Baillieve, Tindall & Cox. Ltd. London, 1961, page 1303. L-DOPA was given at the fixed dose of 100 mg/kg. Trazodone and etoperidone were studied at different doses. This adrenergic inhibition by trazodone and etoperidone is being described for the first time in this patent application. The method used may be described as follows: groups of 3 mice were injected with mg. of either trazodone or etoperidone 5 min. before a fixed dose of 100 mg. L-DOPA and placed in Perspex cages (15×39×24). The animals had no access to either food or water during the experimental session. Each mouse was scored for the presence of piloerection and mydriasis at 5 min. intervals for 30 min. Piloerection and mydriasis were assessed according to the scoring system of Irwin (1964).

Results obtained in Tables I and II show that trazodone and etoperidone inhibit the adrenergic effects of L-DOPA, the effective doses being in the ratio of about 1:12 with respect to L-DOPA.

The synergism between trazodone or etoperidone and L-DOPA was studied by administering a fixed dose of the first ones (3.12 mg/kg) and increasing doses of L-DOPA.

The effects of trazodone and L-DOPA, both alone and combined, on oxotremorine induced tremor are summarized in FIG. 1.

FIG. 1

Results show a synergism of effects; in fact the experimental points of the drug combination show a curvilinear regression, which lies above the straight line of L-DOPA, chosen as the reference agent.

Results obtained in the oxotremorine test with L-DOPA and etoperidone, both alone and combined, are shown in FIG. 2.

FIG. 2

The effects of etoperidone and L-DOPA were quite similar to those obtained with trazodone and L-DOPA and again a synergism was shown between the 2 drugs.

The acute toxicity of L-DOPA, both alone and combined with etoperidone or trazodone is known in Table III.

Trazodone and etoperidone were administered at a fixed dose of 50 mg/kg. Results obtained show that the acute toxicity of L-DOPA is not significantly changed by the simultaneous administration of trazodone or etoperidone there with.

On the basis of results obtained in animals a clinical trial was started in 20 Parkinsonian patients. Trazodone and etoperidone were combined with L-DOPA in the ratio of 1:20. The study was performed using capsules containing trazodone or etoperidone, combined with L-DOPA, at the following doses:

| Trazodone or etoperidone | L-DOPA |
|---|---|
| 12.5 | 250 |
| — | — |
| 25 | 500 |
| 50 | 1000 |

No difference was observed when the drug combinations trazodone-L-DOPA or etoperidone-L-DOPA were given in the form of 1 capsule containing the two active ingredients or 1 capsule containing a mixture of the two active ingredients. The capsules were given 4 times daily. The treatment was started with the lower dose and was gradually increased at weekly intervals until a satisfactory theraputic effect was reached. A similar group of ten patients was treated with L-DOPA alone, according to the dosage scheme indicated above. The symptoms of the patients were scored from 1 to 5. The tolerance was evaluated on the basis of routine laboratory tests, blood pressure, heart rate, ECG, EEG, and the subjective evaluation of the patient. Results obtained have shown that the combination of L-DOPA with trazodone or etoperidone produces a therapeutic action in Parkinsonism at lower doses and with a lower incidence of side effects than with L-DOPA alone. In fact, a satisfactory therapeutic action was reached during the second week, when the daily dose was 100 mg of trazodone or etoperidone and 2 g of L-DOPA, or during the third week when the daily dose was 200 mg of trazodone or etoperidone and 4 g of L-DOPA. These active doses should be compared with those of L-DOPA alone, which are considerably higher. On the basis of this study it may be concluded that the range of daily therapeutic doses of the combination applied for in the present Patent is from 100 to 200 mg of trazodone or etoperidone and from 2 to 4 g of L-DOPA.

TABLE I

Effects of trazodone on L-DOPA — induced piloerection and mydriasis in mice. L-DOPA was administered at a fixed dose of 100 mg/kg i.p.

| Trazodone (mg/kg) p.o. | Percentage Inhibition | |
|---|---|---|
| | Piloerection | Mydriasis |
| 3.12 | 13 | — |
| 6.25 | 27[1] | 19[2] |
| 12.5 | 52[2] | — |

[1] and [2] significant at $P<0.01$ and $P<0.001$ respectively.

TABLE II

Effects of etoperidone on L-DOPA — induced piloerection and mydriasis in mice. L-DOPA was administered at a fixed dose of 100 mg/kg i.p.

| Etoperidone (mg/kg) p.o. | Percentage Inhibition | |
| --- | --- | --- |
| | Piloerection | Mydriasis |
| 3.12 | 18 | — |
| 6.25 | 30[1] | 24[2] |
| 12.5 | 72[2] | — |

[1] and [2] significant at $P<0.01$ and $P<0.001$ respectively.

TABLE III

Acute toxicity of L-DOPA in mice, both alone and combined with trazodone or etoperidone. Trazodone and etoperidone were administered 30 min. before L-DOPA.

| Drugs | Doses mg/kg p.o. | No. of mice | $LD_{50}$ of L-DOPA (mg/kg i.p.) | S |
| --- | --- | --- | --- | --- |
| — | | 158 | 2290 (2009 – 2610) | 1.5 |
| trazodone | 50 | 72 | 2180 (1708 – 2325) | 1.9 |
| etoperidone | 50 | 72 | 1900 (1553 – 2325) | 1.5 |

I claim:

1. A method of treatment of Parkinsonism comprising administering to a patient a combination of trazodone with L-DOPA or etoperidone with L-DOPA at a daily oral dose of 100 to 200 mg of trazodone or etoperidone and a daily dose of 2 to 4 g of L-DOPA substantially in a ratio of 1 part of trazodone or etoperidone for 12 to 25 parts of L-DOPA.

2. A method of treatment according to claim 1, wherein said treatment is carried out at a ratio of about 12 parts to about 25 parts of L-DOPA for every part of trazodone or etoperidone being administered.

3. A method of treatment according to claim 1, wherein said L-DOPA is administered separately from said trazodone or from said etoperidone for said combination treatment or wherein said L-DOPA is administered together with said trazodone or etoperidone for said combination treatment.

4. A treatment according to claim 3, wherein the combined drugs are substantially in the ratio of 1:20.